United States Patent [19]

Felix

[11] 4,356,026

[45] Oct. 26, 1982

[54] SUBSTITUTED CYCLOPROPYLMETHOXY PHENYL UREAS AND THEIR USE AS HERBICIDES

[75] Inventor: Raymond A. Felix, Richmond, Calif.

[73] Assignee: Stauffer Chemical Company, Westport, Conn.

[21] Appl. No.: 114,539

[22] Filed: Jan. 23, 1980

Related U.S. Application Data

[60] Continuation-in-part of Ser. No. 12,992, Feb. 21, 1979, abandoned, which is a division of Ser. No. 807,940, Jun. 21, 1977, Pat. No. 4,149,874.

[51] Int. Cl.³ .................... A01N 47/30; C07C 127/19; C07C 83/10
[52] U.S. Cl. .......................................... 71/120; 564/45; 564/52; 260/453 RW
[58] Field of Search ..... 71/120; 260/553 A, 453 RW; 564/45, 52

[56] References Cited

U.S. PATENT DOCUMENTS

| | | | |
|---|---|---|---|
| 3,332,768 | 7/1967 | Freund et al. | 71/118 |
| 3,362,992 | 1/1968 | Schwartz | 260/557 |
| 3,555,091 | 1/1971 | Benoit-Guyod | 260/562 A |
| 3,758,579 | 9/1973 | Martin et al. | 260/562 B |
| 3,786,090 | 1/1974 | Hussain | 260/562 A |
| 3,834,446 | 10/1974 | Teach | 260/562 A |
| 3,875,229 | 4/1975 | Gold | 260/562 R |
| 3,885,948 | 5/1975 | Baker et al. | 71/67 |
| 3,987,059 | 10/1976 | Houlihan | 260/325.16 |
| 4,013,452 | 3/1977 | Scherer et al. | 71/120 |
| 4,144,049 | 3/1979 | Yoshida et al. | 71/120 |
| 4,153,448 | 5/1979 | Cross | 71/120 |

FOREIGN PATENT DOCUMENTS

| | | |
|---|---|---|
| 7803787 | 1/1979 | Brazil . |
| 324 | 1/1979 | European Pat. Off. . |
| 1219947 | 6/1966 | Fed. Rep. of Germany . |

Primary Examiner—Catherine L. Mills
Attorney, Agent, or Firm—Joel G. Ackerman

[57] ABSTRACT

Compounds having the formula

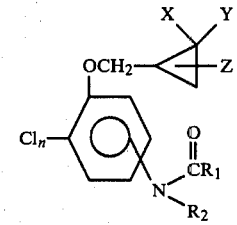

in which $R_1$ is alkyl, lower alkenyl, chloro-lower alkyl, lower cycloalkyl, lower alkoxy, thio-lower alkyl, or

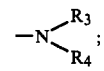

$R_2$ is hydrogen, lower alkoxyalkyl or lower alkanoyl; $R_3$ and $R_4$ are independently hydrogen, lower alkyl or lower alkoxy; X and Y are independently chloro, fluoro or bromo; Z is hydrogen, methyl, dimethyl or one methyl and one chloro substituent; and n is 0 or 1. The compounds have utility as herbicides, particularly as post-emergence herbicides.

53 Claims, No Drawings

SUBSTITUTED CYCLOPROPYLMETHOXY PHENYL UREAS AND THEIR USE AS HERBICIDES

CROSS-REFERENCE TO RELATED APPLICATIONS

This is a continuation-in-part of Application Ser. No. 12,992, filed Feb. 21, 1979, now abandoned which is a division of Application Ser. No. 807,940, filed June 21, 1977, now U.S. Pat. No. 4,149,874.

SUMMARY OF THE INVENTION

This invention relates to novel herbicidal compounds having the formula

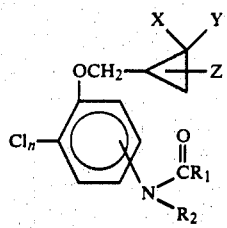

in which $R_1$ is alkyl, lower alkenyl, chloro-lower alkyl, lower cycloalkyl, lower alkoxy, thio-lower alkyl, or

$R_2$ is hydrogen, lower alkoxyalkyl or lower alkanoyl; $R_3$ and $R_4$ are independently hydrogen, lower alkyl or lower alkoxy; X and Y are independently chloro, fluoro or bromo; Z is hydrogen, methyl, dimethyl, or one methyl and one chloro substituent; and n is 0 or 1, provided that if n is 1, $R_1$ is alkyl and $R_2$ is hydrogen, then $R_1$ is an alkyl group having from 1 to 4 carbon atoms.

By the term "alkyl" is meant such groups having from 1 to 10, preferably from 1 to 6 carbon atoms, including both straight chain and branched chain groups. Examples of alkyl groups are methyl, ethyl, n-propyl, isopropyl, butyl, 1-methylbutyl, and 1,1-dimethylbutyl groups.

By the terms "lower alkyl", "chloro-lower alkyl", "lower alkoxy", "thio-lower alkyl", "lower alkoxyalkyl" and "lower alkanoyl", are meant such groups having from 1 to 4 carbon atoms. Examples of such groups are methyl, ethyl, isopropyl, n-butyl, methoxy, isopropoxy, α-chloroethyl, thioethyl, ethoxymethyl, propionyl, and the like.

By the term "lower alkenyl" is meant such groups having from 2 to 4 carbon atoms, for example, propenyl and isopropenyl.

By the term "lower cycloalkyl" is meant such groups having from 3 to 5 carbon atoms. A preferred member of this group is cyclopropyl.

In one embodiment of this invention, the compounds are ureas; that is $R_1$ is

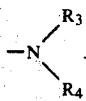

In another embodiment, $R_1$ is alkyl, lower alkenyl, chloro-lower alkyl or lower cycloalkyl; the compounds are mono-amides; if $R_1$ is lower alkoxy the compounds are carbamates; if $R_1$ is thio-lower alkyl, they are thiocarbamates. If $R_1$ is as defined in the previous sentence, the nitrogen-containing group is referred to as the "amide moiety". If $R_1$ is an amide moiety and $R_2$ is lower alkanoyl, the compounds are imides. $R_2$ is preferably hydrogen.

In one embodiment of the invention, the amide or urea moiety and the halo-substituted cyclopropylmethoxy moiety are substituted on the phenyl ring in the meta position with respect to each other. In another embodiment the two moieties are substituted on the phenyl ring in the para position with respect to each other. In a third embodiment, the two moieties are substituted on the phenyl ring in the para position with respect to each other and a mono-chloro group is substituted on the phenyl ring in the ortho position with respect to the cyclopropylmethoxy substituent. This embodiment inlcudes many of the most active compounds of this invention.

In another embodiment of the invention, X and Y are both chloro. In yet another embodiment of the invention, X is chloro and Y is bromo or fluoro. In still another embodiment of the invention, X and Y are both chloro and Z is 1-methyl. In another embodiment of the invention, Z is 3-chloro, 3-methyl.

The compounds of this invention have been found, in general, to be active herbicides; that is, they have been found to be herbicidally effective against various weeds. Weeds, in the broadest sense are plants which grow in locations in which they are not desired. The compounds of this invention have varied herbicidal activities; that is, the effect of the compounds on weeds differs according to the structure, with regard to pre- and post-emergence activity and grassy versus broadleafed plant response, as well as varied responses between species. In general, the compounds of this invention show at best only moderate general activity as pre-emergence herbicides but are primarily active as post-emergence herbicides at rates of application of up to about 8 pounds per acre or higher. In general, as both pre-emergence and post-emergence herbicides, the compounds are active primarily against broadleaf weeds; some of the compounds of this invention are active against both broadleaf and grass weeds as post-emergence herbicides.

These novel compounds may be employed as both general and selective herbicides. When employed at high rates they can be used as total weedkillers in places when complete or near complete destruction of vegetation is needed, for example, on railroad trackbeds, shoulders and median strips of highways, vacant lots, etc. When used at lower rates, the compounds may be satisfactory as selective herbicides; several of these compounds have been shown selective control of broadleaf weeds in small grain crops such as wheat and barley, even when applied at low rates.

It will be seen from the data given in Tables II and III that the compounds in which $R_1$ is lower alkoxy or thio-lower alkyl appear to be less active as a general matter than the corresponding alkyl compounds.

An herbicide as used herein, means a compound which controls or modifies the growth of plants. By the term "herbicidally effective amount" is meant an amount of the compound which causes a modifying effect upon the growth of plants. By "plants" is meant germinant seeds, emerging seedlings, and established vegetation, including roots and above-ground portions. Such modifying effects include all deviations from development, for example, killing, retardation, defoliation, desiccation, regulation, stunting, tillering, stimulation, leaf burn, dwarfing, and the like.

Therefore, in another aspect, this invention relates to herbicidal compositions of matter employing the compounds of the present invention in admixture with an inert diluent or carrier. In another aspect, this invention relates to a method for controlling undesirable vegetation comprising applying to the locus thereof an herbicidally effective amount of a compound of the present invention. In a preferred embodiment of this aspect, the compound is applied subsequent to the emergence of the undesired vegetation at the locus.

In general, the compounds of the present invention are prepared by:

(a) reaction of a hydroxyaniline with a substituted cyclopropylmethyl halide:

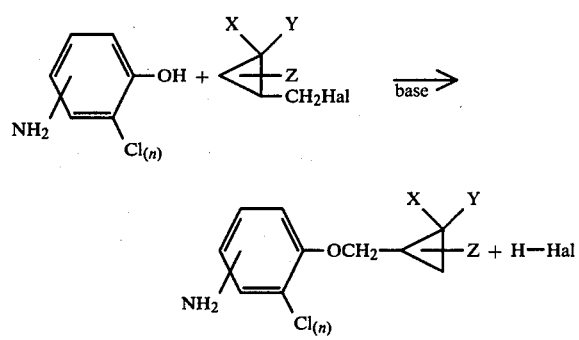

The product of step (a) is then converted to the amine or urea in one or two steps. The amine can be produced in one step by simple acylation:

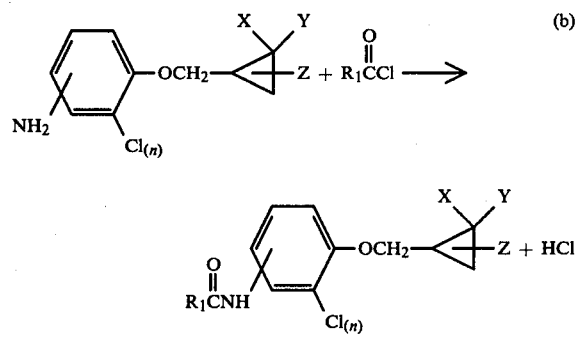

To form the ureas, the product of reaction (a) is preferably first reacted with phosgene instead of an acyl halide, to form an isocyanate, which is then reacted with an appropriate amine or alcohol to form the urea:

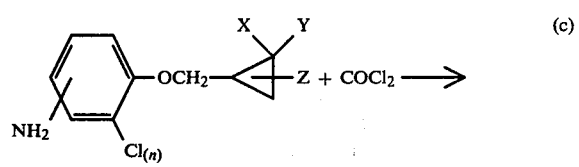

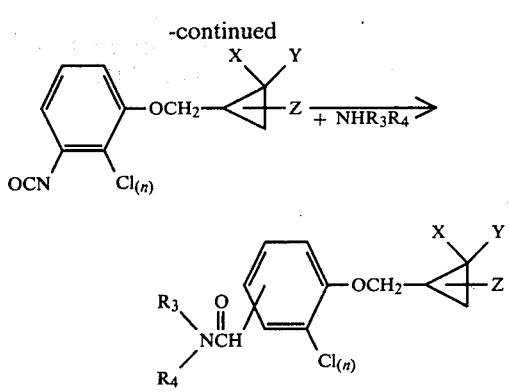

The imides ($R_2$ is lower alkonoyl) can be made from the amides by further acylation with an acyl chloride.

The compounds in which $R_2$ is lower alkoxyalkyl can be made by reacting the amides with sodium hydride, followed by reaction with a halo alkyl ether, such as chloromethyl ethyl ether.

Reaction (a) can be enhanced by the use of a phase transfer catalyst such as a quaternary onium salt.

The following represent examples of preparation of compounds of the present invention. cl EXAMPLE 1

Preparation of N-3-(2',2'-dichloro-1'-methylcyclopropylmethoxy)phenyl cyclopropanecarboxylic acid (Compound 15 herein)

In a flask were placed 181 g. (2 moles) of methallyl chloride, 358 g. (3 moles) of chloroform and 3 g. (0.01 mole) of tetrabutyl phosphonium chloride. There was then added 9 moles of 50% sodium hydroxide solution, dropwise over two hours with vigorous stirring. After the addition was complete, the reaction mixture was stirred for four hours at 30° C. and then poured into two liters of water and extracted with methylene chloride. Distillation at 25 mm. gave 269 g. (77% yield) of 1,1-dichloro-2-chloromethyl-2-methylcyclopropane, b.p. 65°–70° C.

51 g. (0.3 mole) of the compound prepared in the previous step was placed in a flask and mixed with 40 g. (0.37 mole) of 3-aminophenol, 60 g. (0.75 mole) of 50% sodium hydroxide solution, 30 ml. of water and 2 g. of tetrabutylphosphonium chloride. The reaction mixtures was then heated to reflux with stirring for three hours, and then poured into 1 liter of water and extracted with methylene chloride. The extract was dried and methylene chloride stripped off at reduced pressure to yield 69 g. (93%) of 3-(2,2-dichloro-1-methylcyclopropyl)methoxyaniline, a dark amber oil.

In a third flask there were placed 2.5 g. (0.01 mole) of the compound prepared in the previous step, together with 1.05 g. (0.01 mole) of cyclopropanecarboxylic acid chloride, 1.01 g. (0.01 mole) of triethylamine and 25 ml. of ether. The flask was maintained at 5° C. during the filling with reactants. The reaction mixture was then stirred for two hours, poured into water and extracted with ether. The ether extract was washed successively with 1 M. hydrochloric acid and 1 M. sodium hydroxide, dried and stripped. There was obtained 2.5 g. (% of theoretical) of the desired compound, $n_D{}^{30}$. The structure was confirmed by spectroscopic analyses.

EXAMPLE 2

Preparation of 3-(2',2'-dichloro-1'-methyl cyclopropylmethoxy)-2-methyl propionanilide (Compound 11 herein)

There were combined 2.5 g. (0.01 mole) 3-(2',2'-dichloro-1'-methyl-cyclopropylmethoxy)aniline, 1.07 g. (0.01 mole) isobutyryl chloride, 1.5 ml. (0.01 mole) triethylamine and 25 ml. ether. During the mixing, the temperature was maintained at 0° C. The mixture was stirred for 2 hours at room temperature; water was added and the mixture extracted with ether. The organic layer was dried and the ether removed under reduced pressure. There was obtained 2.8 g. of the desired compound, $n_D^{30}$ 1.5141.

EXAMPLE 3

Preparation of N,N-dimethyl-N'[3-(2'',2'''-dichloro-1'''-methylcyclopropylmethoxy)phenyl]urea (Compound 6 herein)

25 g. (0.1 mole) 3-(2',2'-dichloro-1'-methylcyclopropylmethoxy)aniline was dissolved in 150 ml. benzene. The solution was saturated with gaseous HCl and 100 ml. of a 12.5% solution of phosgene in benzene was added. The solution was refluxed for 3 hours, then cooled. The solvent was removed under reduced pressure. To the product of this reaction, 3(2',2'-dichloro-1'-methylcyclopropylmethoxy)phenyl isocyanate, 200 ml. methylene chloride was added and gaseous dimethylamine was bubbled in for ½ hour. The solution was stirred for ½ hour at room temperature, then the solvent was removed under reduced pressure. The residue was slurried in a 25% solution of ether in hexane. There was obtained 22 g. of the desired product, a white solid, m.p. 99°–101° C.

EXAMPLE 4

Preparation of N-[3-(2',2'-dichloro-1'-methylcyclopropylmethoxy)-phenyl]0-isopropyl carbamate (Compound 9 herein)

4.1 g. (0.015 mole) 3-(2',2'-dichloro-1'-methylcyclopropylmethoxy)phenyl isocyanate was dissolved in 20 ml. methylene chloride. Then, 2 g. isopropanol was added and the solution stirred for 4 hours. The solvents were removed under reduced pressure to yield 5 g. of the desired compound as an oil, $n_D^{30}$ 1.5072.

EXAMPLE 5

Preparation of O-ethyl-N-3-(2',2'-dichloro-1'-methylcyclopropylmethoxy)phenyl carbamate (Compound 21 herein)

A solution was formed by dissolving 6.5 g. (0.03 mole) 3-(2',2'-dichloro-1'-methylcyploroylmethoxy)aniline, 3.2 g. (0.03 mole) ethyl chloroformate and 3.1 g. (0.031 mole) triethylamine in 50 ml. benzene. The solution was refluxed for 3 hours and cooled. Methylene chloride was added and the organic layer was washed with water, dried and evaporated. There was obtained 8.7 g. of the desired product, $n_D^{30}$ 1.5113.

EXAMPLE 6

Preparation of 3-(2''-chloro-2''-fluoro-1''-methylcyclopropylmethoxy),2',2'-dimethyl valeranilide (Compound 24 herein)

There were combined 5.0 g. (0.0226 mole) N-3-hydroxyphenyl-2,2-dimethylvaleramide, 3.15 g. (0.02 mole) 1-chloro-1-fluoro-2-chloromethyl-2-methyl cyclopropane, 2.0 g. (0.025 mole) of a 50% caustic solution, 2 ml. water and 300 mg. tetrabutyl phosphonium chloride. The mixture was refluxed for 2 hours; water was then added and the mixture extracted with methylene chloride. The organic layer dried and evaporated to yield 4.2 g. of the desired product, $n_D^{30}$ 1.4679.

The following Table I lists representative compounds of the present invention:

TABLE I

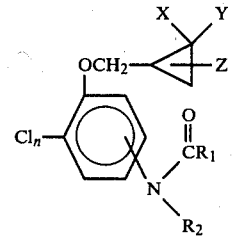

| Compound No. | $R_1$ | $R_2$ | X | Y | Z | Relative* Position | n | m.p. or $n_D^{30}$ |
|---|---|---|---|---|---|---|---|---|
| 1 | $C_2H_5$ | H | Cl | Cl | H | meta | 0 | 115–118° C. |
| 2 | $C_2H_5$ | H | Cl | Cl | 1-$CH_3$ | meta | 0 | 1.5230 |
| 3 | $\begin{array}{c}CH_3\\|\\-C-CH\\|\\CH_3\end{array}$ | H | Cl | Cl | 1-$CH_3$ | meta | 0 | 75–78° C. |
| 4 | $C_2H_5$ | H | Cl | Cl | 3,3-$CH_3$ | meta | 0 | 1.5130 |
| 5 | $-CHClCH_3$ | H | Cl | Cl | 1-$CH_3$ | meta | 0 | 1.5173 |
| 6 | $-N(CH_3)_2$ | H | Cl | Cl | 1-$CH_3$ | meta | 0 | 100–104° C. |
| 7 | $-NHCH_3$ | H | Cl | Cl | 1-$CH_3$ |  | 0 | (glass) |

TABLE I-continued

[Structure: Phenyl ring with OCH₂-cyclopropane (bearing X, Y, Z substituents), Cl_n substituent, and N(R₂)-C(=O)-R₁ group]

| Compound No. | R₁ | R₂ | X | Y | Z | Relative* Position | n | m.p. or $n_D^{30}$ |
|---|---|---|---|---|---|---|---|---|
| 8 | -N(CH₃)(OCH₃) | H | Cl | Cl | 1-CH₃ | meta | 0 | 105-108° C. |
| 9 | -O-CH(CH₃)₂ | H | Cl | Cl | 1-CH₃ | meta | 0 | 1.5072 |
| 10 | -NH-C(CH₃)₃ | H | Cl | Cl | 1-CH₃ | meta | 0 | (glass) |
| 11 | i-C₃H₇ | H | Cl | Cl | 1-CH₃ | meta | 0 | 1.5141 |
| 12 | -C(CH₃)=CH₂ | H | Cl | Cl | 1-CH₃ | meta | 0 | 1.5199 |
| 13 | -CH=CHCH₃ | H | Cl | Cl | 1-CH₃ | meta | 0 | 1.5158 |
| 14 | CH₃ | H | Cl | Cl | 1-CH₃ | meta | 0 | 1.5251 |
| 15 | cyclopropyl | H | Cl | Cl | 1-CH₃ | meta | 0 | (glass) |
| 16 | sec.-C₄H₉ | H | Cl | Cl | 1-CH₃ | meta | 0 | 1.5038 |
| 17 | n-C₃H₇ | H | Cl | Cl | 1-CH₃ | meta | 0 | 1.5509 |
| 18 | C₂H₅ | H | Cl | Cl | 1-CH₃ | para | 0 | 1.5612 |
| 19 | NH(n-C₄H₉) | H | Cl | Cl | 1-CH₃ | meta | 0 | (thick glass) |
| 20 | NH(n-C₄H₉) | H | Cl | F | 1-CH₃ | meta | 0 | (crude solid) |
| 21 | OC₂H₅ | H | Cl | Cl | 1-CH₃ | meta | 0 | 1.5113 |
| 22 | -C(CH₃)₂-C₃H₇ | H | Br | Br | 1-CH₃ | meta | 0 | 1.5120 |
| 23 | -C(CH₃)₂-C₃H₇ | H | Cl | Br | 1-CH₃ | meta | 0 | 1.4938 |
| 24 | -C(CH₃)₂-C₃H₇ | H | Cl | F | 1-CH₃ | meta | 0 | 1.4679 |
| 25 | -C(CH₃)₂-C₃H₇ | H | Cl | Cl | H | meta | 0 | 1.5079 |
| 26 | -C(CH₃)₂-C₃H₇ | H | Cl | Cl | 3-Cl,3-CH₃ | meta | 0 | 1.5017 |
| 27 | -CH=CHCH₃ | H | Cl | Cl | 1-CH₃ | para | 1 | (thick glass) |
| 28 | -C(CH₃)=CH₂ | H | Cl | Cl | 1-CH₃ | para | 1 | (semi-solid) |

TABLE I-continued

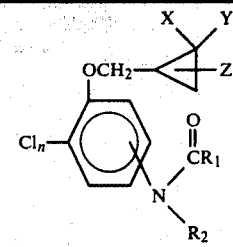

| Compound No. | $R_1$ | $R_2$ | X | Y | Z | Relative* Position | n | m.p. or $n_D^{30}$ |
|---|---|---|---|---|---|---|---|---|
| 29 | —◁ | H | Cl | Cl | 1-CH$_3$ | para | 1 | 118–121° C. |
| 30 | C$_2$H$_5$ | H | Cl | Cl | 1-CH$_3$ | para | 1 | 1.5253 |
| 31 | i-C$_3$H$_7$ | H | Cl | Cl | 1-CH$_3$ | para | 1 | 1.5102 |
| 32 | SC$_2$H$_5$ | H | Cl | Cl | 1-CH$_3$ | para | 1 | 85–87° C. |
| 33 | n-C$_3$H$_7$ | H | Cl | Cl | 1-CH$_3$ | para | 1 | 1.5202 |
| 34 | sec.-C$_4$H$_9$ | H | Cl | Cl | 1-CH$_3$ | para | 1 | 109–112° C. |
| 35 | —C(CH$_3$)$_2$—C$_3$H$_7$ | H | Cl | Cl | 1-CH$_3$ | para | 1 | 128–130° C. |
| 36 | SC$_2$H$_5$ | H | Cl | Cl | 1-CH$_3$ | meta | 0 | (sticky solid) |
| 37 | —◁ | CH$_2$OC$_2$H$_5$ | Cl | Cl | 1-CH$_3$ | para | 1 | 1.5202 |
| 38 | —◁ | H | Cl | Cl | H | meta | 0 | 1.5370 |
| 39 | C$_2$H$_5$ | COC$_2$H$_5$ | Cl | Cl | 1-CH$_3$ | para | 1 | 1.5152 |
| 40 | —◁ | H | Cl | Cl | 3,3-CH$_3$ | para | 1 | (crude solid) |
| 41 | N(CH$_3$)(OCH$_3$) | H | Cl | Cl | 1-CH$_3$ | para | 1 | 1.5303 |
| 42 | N(CH$_3$)$_2$ | H | Cl | Cl | 1-CH$_3$ | para | 1 | thick glass |
| 43 | NHCH(CH$_3$)$_2$ | H | Cl | Cl | 1-CH$_3$ | para | 1 | thick glass |
| 44 | N(C$_2$H$_5$)$_2$ | H | Cl | Cl | 1-CH$_3$ | meta | 0 | 90–94° C. |
| 45 | N[CH(CH$_3$)$_2$]$_2$ | H | Cl | Cl | 1-CH$_3$ | meta | 0 | 101–103° C. |
| 46 | N(CH$_3$)(n-C$_4$H$_9$) | H | Cl | Cl | 1-CH$_3$ | meta | 0 | 72–74° C. |
| 47 | NHC$_2$H$_5$ | H | Cl | Cl | 1-CH$_3$ | meta | 0 | 1.5392 |
| 48 | N(CH$_3$)$_2$ | H | Cl | Cl | 3,3-CH$_3$ | meta | 0 | 114–116° C. |
| 49 | NHCH(CH$_3$)$_2$ | H | Cl | Cl | 3,3-CH$_3$ | meta | 0 | 129–135° C. |
| 50 | N(CH$_3$)$_2$ | H | Cl | F | 1-CH$_3$ | meta | 0 | 125–131° C. |
| 51 | N(CH$_3$)$_2$ | H | Br | Br | 1-CH$_3$ | meta | 0 | 89–92° C. |
| 52 | N(CH$_3$)$_2$ | H | Cl | Br | 1-CH$_3$ | meta | 0 | 89–91° C. |
| 53 | N(CH$_3$)$_2$ | H | Cl | Cl | H | meta | 0 | waxy solid |

*of cyclopropylmethoxy and amide or urea moieties on phenyl ring.

HERBICIDAL SCREENING TESTS

The representative compounds in the foregoing Table I were tested as herbicides in the following manner:

A. Pre-emergence Herbicide Screening Test: (8 lb./acre)

Using an analytical balance, 20 mg. of the compound to be tested was weighed out on a piece of glassine weighing paper. The paper and compound were placed in a 30-ml. wide-mouth bottle and 3 ml. of acetone containing 1% polyoxyethylene sorbitan monolaurate emulsifier was added to dissolve the compound. If the material was not soluble in acetone, another solvent such as water, alcohol or dimethylformamide (DMF) was used instead. When DMF was used, only 0.5 ml. or less was used to dissolve the compound and then another solvent was used to make the volume up to 3 ml. The 3 ml. solution was sprayed uniformly on the soil contained in a polystyrene flat, 7 inches long, 5 inches wide and 2.75 inches deep one day after planting weed seeds in the flat of soil. A No. 152 DeVilbiss atomizer was used to apply the spray using compressed air at a pressure of 5 lb./sq. in. The rate of application was 8 lb./acre and the spray volume was 143 gal./acre.

On the day preceding treatment, the flat was filled to a depth of 2 inches with loamy sand soil. Seeds of seven different weed species were planted in individual rows one species per row across the width of the flat. The seeds were covered with soil so that they were planted at a depth of 0.5 inch. The seeds used were those of four grasses: hairy crabgrass (*Digitaria sanguinalis*), yellow foxtail (*Setaria glauca*), watergrass (*Echinochloa crusgalli*), red oat (*Avena sativa*), and three broadleaf weeds: redroot pigweed (Amranthus retroflexus), Indian mustard (*Brassica juncea*) and curly dock (*Rumex crispus*). Ample seeds were planted to give about 20 to 50 seedlings per row after emergence depending on the size of the plants.

After treatment, the flats were placed in the greenhouse at a temperature of 70° to 85° F. and watered by sprinkling. Two weeks after treatment the degree of injury or control was determined by comparison with untreated check plants of the same age. The injury rating from 0 to 100% was recorded for each species as percent control with 0% representing no injury and 100% representing complete kill. Results of these tests are shown in the following Table II.

TABLE II

| Pre-Emergence Control (Rate: 8 lb./acre) | | |
|---|---|---|
| Compound No. | Grasses* | Broadleaf Weeds** |
| 1 | 0 | 13 |
| 2 | 0 | 17 |
| 3 | 5 | 94 |
| 4 | 0 | 48 |
| 5 | 0 | 0 |
| 6 | 34 | 95 |
| 7 | 23 | 90 |
| 8 | 43 | 98.5 |
| 9 | 0 | 0 |
| 10 | 0 | 43 |
| 11 | 0 | 0 |
| 12 | 0 | 3 |
| 13 | 0 | 0 |
| 14 | 0 | 10 |
| 15 | 0 | 0 |
| 16 | 0 | 0 |
| 17 | 0 | 0 |
| 18 | 0 | 0 |
| 19 | 0 | 0 |
| 20 | 0 | 90 |
| 21 | 0 | 22 |
| 22 | 0 | 10 |
| 23 | 0 | 17 |
| 24 | 0 | 72 |
| 25 | 30 | 85 |
| 26 | 0 | 0 |
| 27 | 0 | 20 |
| 28 | 0 | 66 |
| 29 | 15 | 97 |
| 30 | 0 | 49 |
| 31 | 5 | 90 |
| 32 | 0 | 0 |
| 33 | 0 | 45 |
| 34 | 0 | 23 |
| 35 | 0 | 0 |
| 36 | 0 | 0 |
| 37 | 0 | 20 |
| 38 | 0 | 0 |
| 39 | 0 | 100 |
| 40 | 0 | 0 |
| 41 | 49 | 76 |
| 42 | 3 | 46 |
| 43 | 0 | 10 |

*Average control for 4 grasses
**Average control for 3 broadleaf weeds.

B. Post-emergence Herbicide Screening Test: (8 lb./acre)

Seeds of six plant species, including three grasses: hairy crabgrass, watergrass, red oat and three broadleaf weeds: mustard, curly dock and pinto beans (*Phaseolus vulgaris*) were planted in the flats as described above for pre-emergence screening. The flats were placed in the green house at 70° to 85° F. and watered daily with a sprinkler. About 10 to 14 days after planting when the primary leaves of the bean plants were almost fully expanded and the first trifoliate leaves were just starting to form, the plants were sprayed. The spray was prepared by weighing out 20 mg. of the test compound, dissolving it in 5 ml. of acetone containing 1% polyoxyethylene sorbitan monolaurate and then adding 5 ml. of water. The solution was sprayed on the foliage using a No. 152 DeVilbiss atomizer at an air pressure of 5 lb./sq. in. The spray concentration was 0.2% and the rate was 8 lb./acre. The spray volume was 476 gal./acre. Results of these tests are shown in Table III.

TABLE III

| Post-Emergence Control (Rate: 8 lb./acre) | | |
|---|---|---|
| Compound No. | Grasses* | Broadleaf Weeds** |
| 1 | 83 | 100 |
| 2 | 56 | 100 |
| 3 | 50 | 100 |
| 4 | 63 | 100 |
| 5 | 30 | 67 |
| 6 | 80 | 100 |
| 7 | 33 | 67 |
| 8 | 63 | 100 |
| 9 | 0 | 67 |
| 36 | 0 | 71 |
| 37 | 60 | 100 |
| 38 | 93 | 100 |
| 39 | 77 | 100 |
| 40 | 99 | 100 |
| 41 | 63 | 100 |
| 42 | 60 | 100 |
| 43 | 17 | 87 |

*Average control for 3 grasses
**Average control for 3 broadleaf weeds

C. Pre-Emergence Herbicidal Evaluation: (2 lb./acre)

Galvanized iron flats which are 12 inches long, 8 inches wide and 3 inches deep were filled with 11 pints of sandy loam soil containing 75 ppm cis-N-[(trichloromethyl)thio]-4-cyclohexene-1,2-dicarboximide and 150 ppm 17-17-17 fertilizer. The moisture content is about 9%. The soil was leveled and row markers used to impress seven rows across the width of the flat. Full rows of foxtail (*Setaria spp.*), watergrass (*Echinocloa crusgalli*), wild oats (*Avena fatua*), mustard (*Brassica*

*juncea*), curly dock (*Rumex crispus*) and pigweed (*Amaranthus retroflexus*) were planted thick enough so that several seedlings emerged per inch of row. The flats were placed in a greenhouse at 70°–85° F. and watered by sprinkling. One day after planting, the flats were sprayed at a rate of 80 gallons of solution per acre. The compound was applied at the rate of 2 lb./acre.

The spray solution was made up by weighing out 300 mg. of the compound into a 120 ml. wide-mouth bottle, dissolving it in 50 ml. of acetone containing 1%, polyoxyethylene sorbitan monolaurate emulsifier and then diluting to 100 ml. with water. Additional solvents, not to exceed 5 ml. were used if needed to dissolve the compound.

The flats were returned to the greenhouse after spraying and watered daily by sprinkling. Three weeks after treatment, the degree of weed control was estimated and recorded as percentage control compared to the growth of the same species in an untreated check flat of the same age.

The percent control is based on the total injury to the plants due to all factors including inhibited germination, killing of the plant tissue after emergence, stunting, malformation, chlorosis and other types of injury. The control ratings vary from 0 to 100%, where 0 represents no effect with growth equal to the untreated control, and 100 represents complete kill.

Results of these tests are contained in Table IV.

TABLE IV

| Pre-emergence Control (Rate: 2 lb./acre) | | |
|---|---|---|
| Compound No. | Grasses* | Broadleaf Weeds** |
| 44 | 0 | 40 |
| 45 | 0 | 0 |
| 46 | 0 | 20 |
| 47 | 0 | 0 |
| 48 | 0 | 43 |
| 49 | 0 | 0 |
| 50 | 60 | 86 |

*Average control for 3 grasses
**Average control for 3 broadleaf weeds

Compounds 51, 52 and 53 were tested by a similar procedure against a total of seven weeds including 3 grasses (foxtail, watergrass, wild oat) and 4 broadleaf weeds (Annual morningglory, *Ipomoea purpurea;* velvetleaf, *Alutilon theophrasti;* mustard and redroot pigweed). These compounds showed no pre-emergent activity in this test.

D. Post-Emergence Herbicidal Evaluation: (2 lb./acre)

The soil was prepared and seeded as described for the pre-emergence tests. The flats were placed in the greenhouse at 70°–85° F. and watered by sprinkling. Nine to eleven days after planting, the flats were sprayed on a table at a rate of 80 gallons of solution per acre. The compound was applied at the rate of 2 lb./acre.

The spray solution was made up by weighing out 300 mg. of the compound into a 120 ml. wide-mouth bottle, dissolving it in 50 ml. of acetone containing 1% polyoxyethylene sorbitan monolaurate emulsifier and then diluting to 100 ml. with water. Additional solvents were used, up to 5 ml., if needed to dissolve the compound.

The flats were returned to the greenhouse after spraying and watered daily without wetting the foliage for three days. Thereafter, they were watered daily by sprinkling. Three weeks after treatment, the degree of weed control was estimated and recorded as percentage control compared to the growth of the same species in an untreated check flat of the same age.

The percent control is based on the total injury to the plants due to all factors including inhibited germination, killing of the plant tissue after emergence, stunting, malformation, chlorosis and other types of injury. The control ratings vary from 0 to 100%, where 0 represents no effect with growth equal to the untreated control, and 100 represents complete kill.

Results of these tests are shown in Table V.

TABLE V

| Post-emergence Control (Rate: 2 lb./acre) | | |
|---|---|---|
| Compound No. | Grasses* | Broadleaf Weeds** |
| 44 | 40 | 100 |
| 45 | 0 | 87 |
| 46 | 37 | 100 |
| 47 | 30 | 100 |
| 48 | 60 | 100 |
| 49 | 0 | 100 |
| 50 | 100 | 100 |

*Average control of 3 grasses
**Average control of 3 broadleaf weeds

Compounds 51, 52 and 53 were tested for post-emergence activity, by the above procedure, on the same 7 weeds as for pre-emergence activity. The results are shown in Table VI.

TABLE VI

| Post-emergence Control (Rate: 2 lb./acre) | | |
|---|---|---|
| Compound No. | Grasses* | Broadleaf Weeds** |
| 51 | 30 | 98 |
| 52 | 46 | 93 |
| 53 | 33 | 95 |

*Average control of 3 grasses
**Average control of 4 broadleaf weeds

Compounds 44–53 were also tested for pre- and post-emergence control of yellow nutsedge (*Cyperus esculentus*) at 2 lb./acre but did not control this weed.

In practice, a pure compound can be used as a herbicide. However, in general, the compounds are first formulated with one or more inert carriers or diluents suitable for herbicidal use, before being applied.

The compositions or formulations, including a compound as described herein, may take and be used in any one of a number of solid or liquid forms. Examples of solid forms are dusts, granules, tablets, powders and the like. Examples of liquid forms are emulsions, solutions, suspensions, emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; anti-foaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders, flowables and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are also added.

It is possible to use highly concentrated liquid compositions containing up to about 95% by weight of the active compound or even the 100% active compound alone, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes —20 to 90% active compound; oil suspensions, emulsions, solutions and emulsifiable concentrates —5 to 90% active compound; aqueous suspensions —10 to 50% active compounds; dusts and powders —1 to 25% active compound; granules and pellets —1 to 20% active compound.

The rate of application of the active compound to a locus to be controlled will depend on the nature of the seeds and plants to be controlled and will vary from about 0.05 to about 50 pounds per acre (about 0.06 to about 56 kg./ha.).

In addition to the active compound and the various agents utilized in preparing compositions and formulations mentioned above, such compositions may also contain one or more other active compounds of the type mentioned herein as well as other active pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as dusts or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

Compositions applied to the surface of the soil can be distributed below the surface of the soil by conventional means such as discing or mixing operations.

What is claimed is:

1. A compound having the formula

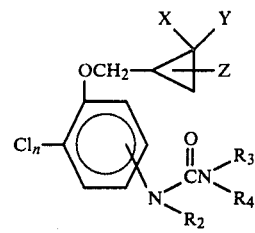

in which $R_2$ is hydrogen, lower alkoxyalkyl or lower alkanoyl; $R_3$ and $R_4$ are independently hydrogen, lower alkyl or lower alkoxy; X and Y are independently chloro, fluoro or bromo; Z is hydrogen, methyl, dimethyl or one methyl and one chloro and substituent; and n is 0 or 1.

2. A compound according to claim 1 in which the cyclopropylmethoxy moiety and the urea moieties are substituted on the phenyl ring in the meta position with respect to each other.

3. A compound according to claim 1 in which the cyclopropylmethoxy moiety and the urea moieties are substituted on the phenyl ring in the para position with respect to each other.

4. A compound according to claim 1 in which n is 1.

5. A compound according to claim 1 in which n is 0.

6. A compound according to claim 5 in which the cyclopropylmethoxy and urea moieties are substituted on the phenyl ring in the meta position with respect to each other.

7. A compound according to claim 1 in which $R_3$ and $R_4$ are both lower alkyl.

8. A compound according to claim 1 in which $R_3$ and $R_4$ are both methyl.

9. A compound according to claim 1 in which $R_3$ is hydrogen and $R_4$ is lower alkyl.

10. A compound according to claim 1 in which $R_3$ is lower alkoxy and $R_4$ is lower alkyl.

11. A compound according to claim 1 in which X and Y are both chloro.

12. A compound according to claim 1 in which X and Y are both bromo.

13. A compound according to claim 1 in which X is chloro and Y is bromo.

14. A compound according to claim 1 in which X is chloro and Y is fluoro.

15. A compound according to claim 1 in which Z is hydrogen.

16. A compound according to claim 1 in which Z is monomethyl.

17. A compound according to claim 1 in which Z is dimethyl.

18. A compound according to claim 1 in which X is chloro, Y is chloro and Z is 1-methyl.

19. A compound according to claim 18 in which n is 0.

20. A compound according to claim 18 in which the cyclopropylmethoxy and urea moieties are substituted on the phenyl ring in the meta position with respect to each other.

21. A compound according to claim 1 in which $R_3$ and $R_4$ are both methyl, $R_2$ is hydrogen, X is chloro, Y is chloro, Z is 1-methyl, n is 0 and the cyclopropylmethoxy and urea moieties are substituted on the phenyl ring in the meta position with respect to each other.

22. A compound according to claim 1 in which $R_2$ is hydrogen, $R_3$ is hydrogen, $R_4$ is methyl, X is chloro, Y is chloro, Z is 1-methyl, n is 0 and the cyclopropylmethoxy and urea moieties are substituted on the phenyl ring in the meta position with respect to each other.

23. A compound according to claim 1 in which $R_2$ is hydrogen, $R_3$ is methoxy, $R_4$ is methyl, X is chloro, Y is chloro, Z is 1-methyl, n is 0 and the cyclopropylmethoxy and urea moieties are substituted on the phenyl ring in the meta position with respect to each other.

24. A compound according to claim 1 in which $R_2$ is hydrogen, $R_3$ is hydrogen, $R_4$ is tert.-butyl, X is chloro, Y is chloro, Z is 1-methyl, n is 0 and the cyclopropylmethoxy and urea moieties are substituted on the phenyl ring in the meta position with respect to each other.

25. A compound according to claim 1 in which $R_2$ is hydrogen, $R_3$ is hydrogen, $R_4$ is n-butyl, X is chloro, Y is chloro, Z is 1-methyl, n is 0 and the cyclopropylmethoxy and urea moieties are substituted on the phenyl ring in the meta position with respect to each other.

26. A compound according to claim 1 in which $R_2$ is hydrogen, $R_3$ is hydrogen, $R_4$ is n-butyl, X is chloro, Y is fluoro, Z is 1-methyl, n is 0 and the cyclopropylmethoxy and urea moieties are substituted on the phenyl ring in the meta position with respect to each other.

27. A method for controlling undesirable vegetation comprising applying to said vegetation or the locus thereof, an herbicidally effective amount of a compound having the formula

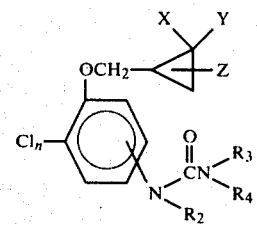

$R_2$ is hydrogen, lower alkoxyalkyl or lower alkanoyl; $R_3$ and $R_4$ are independently hydrogen, lower alkyl or lower alkoxy; X and Y are independently chloro, fluoro or bromo; Z is hydrogen, methyl, dimethyl or one methyl and one chloro substituent; and n is 0 or 1.

28. A method according to claim 27 in which the cyclopropylmethoxy moiety and the urea moieties are substituted on the phenyl ring in the meta position with respect to each other.

29. A method according to claim 27 in which n is 1.

30. A method according to claim 1 in which n is 0.

31. A method according to claim 30 in which the cyclopropylmethoxy and urea moieties are substituted on the phenyl ring in the meta position with respect to each other.

32. A method according to claim 27 in which $R_3$ and $R_4$ are both lower alkyl.

33. A method according to claim 32 in which $R_3$ and $R_4$ are both methyl.

34. A method according to claim 27 in which $R_3$ is hydrogen and $R_4$ is lower alkyl.

35. A method according to claim 27 in which X and Y are both chloro.

36. A method according to claim 27 in which X and Y are both bromo.

37. A method according to claim 27 in which X is chloro and Y is bromo.

38. A method according to claim 27 in which X is chloro and Y is fluoro.

39. A method according to claim 27 in which Z is hydrogen.

40. A method according to claim 27 in which Z is monomethyl.

41. A method according to claim 27 in which Z is dimethyl.

42. A method according to claim 27 in which X is chloro, Y is chloro and Z is 1-methyl.

43. A method according to claim 42 in which n is 0.

44. A method according to claim 43, in which the cyclopropylmethoxy and urea moieties are substituted on the phenyl ring in the meta position with respect to each other.

45. A method according to claim 43 in which the cyclopropylmethoxy and urea moieties are substituted on the phenyl ring in the para position with respect to each other.

46. A method according to claim 27 in which $R_2$ is hydrogen, $R_3$ is methyl, $R_4$ is methyl, X is chloro, Y is chloro, Z is 1-methyl, n is 0 and the cyclopropylmethoxy and urea moieties are substituted on the phenyl ring in the meta position with respect to each other.

47. A method according to claim 27 in which $R_2$ is hydrogen, $R_3$ is methoxy, $R_4$ is methyl, X is chloro, Y is chloro, Z is 1-methyl, n is 0 and the cyclopropylmethoxy and urea moieties are substituted on the phenyl ring in the meta position with respect to each other.

48. A method according to claim 27 in which $R_2$ is hydrogen, $R_3$ is hydrogen, $R_4$ is tert.-butyl, X is chloro, Y is chloro, Z is 1-methyl, n is 0 and the cyclopropylmethoxy and urea moieties are substituted on the phenyl ring in the meta position with respect to each other.

49. A method according to claim 27 in which $R_2$ is hydrogen, $R_3$ is hydrogen, $R_4$ is n-butyl, X is chloro, Y is chloro, Z is 1-methyl, n is 0 and the cyclopropylmethoxy and urea moieties are substituted on the phenyl ring in the meta position with respect to each other.

50. A method according to claim 27 in which $R_2$ is hydrogen, $R_3$ is hydrogen, $R_4$ is n-butyl, X is chloro, Y is fluoro, Z is 1-methyl, n is 0 and the cyclopropylmethoxy and urea moieties are substituted on the phenyl ring in the meta position with respect to each other.

51. A method according to claim 27 in which the compound is applied subsequent to the emergence of the undesirable vegetation.

52. A method according to claim 51 in which the compound is applied to control broadleaf weeds.

53. An herbicidal composition of matter comprising:
(a) an herbicidal amount of a compound having the formula

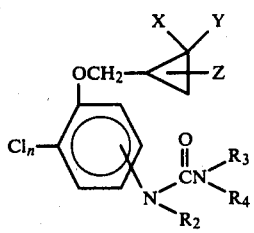
in which $R_2$ is hydrogen, lower alkoxyalkyl or lower alkanoyl; $R_3$ and $R_4$ are independently hydrogen, lower alkyl or lower alkoxy; X and Y are independently chloro, fluoro or bromo; Z is hydrogen, methyl, di-methyl or one methyl and one chloro substituent; and n is 0 or 1, and
(b) an inert diluent or carrier.
* * * * *